US00RE40167E

(19) United States
(12) Reissued Patent
Edwards et al.

(10) Patent Number: US RE40,167 E
(45) Date of Reissued Patent: Mar. 25, 2008

(54) NUCLEAR MAGNETIC RESONANCE FLUID CHARACTERIZATION APPARATUS AND METHOD FOR USING WITH ELECTRIC WIRELINE FORMATION TESTING INSTRUMENTS

(75) Inventors: Carl M. Edwards, Katy, TX (US); Otto N. Fanini, Houston, TX (US); Stanislav W. Forgang, Houston, TX (US)

(73) Assignee: Baker Hughes Incorporated, Houston, TX (US)

(21) Appl. No.: 10/231,412

(22) Filed: Aug. 29, 2002

Related U.S. Patent Documents

Reissue of:
(64) Patent No.: 6,111,409
Issued: Aug. 29, 2000
Appl. No.: 09/033,104
Filed: Mar. 2, 1998

(51) Int. Cl.
*G01V 3/00* (2006.01)
*G01R 33/20* (2006.01)

(52) U.S. Cl. ..... 324/303
(58) Field of Classification Search ..... 324/303, 324/306, 308; 436/29
See application file for complete search history.

(56) References Cited

U.S. PATENT DOCUMENTS

| | | | | | |
|---|---|---|---|---|---|
| 3,439,260 | A | | 4/1969 | Bene | 324/5 |
| 4,477,777 | A | | 10/1984 | Gordon | 324/300 |
| 4,719,582 | A | | 1/1988 | Ishida et al. | 364/498 |
| 4,785,245 | A | * | 11/1988 | Lew et al. | 324/308 |
| 5,306,640 | A | * | 4/1994 | Vinegar et al. | 436/29 |
| 5,363,041 | A | | 11/1994 | Sezginer | 324/303 |
| 5,473,939 | A | | 12/1995 | Leder et al. | 73/155 |
| 5,486,762 | A | * | 1/1996 | Freedman et al. | 324/303 |
| 5,635,631 | A | | 6/1997 | Yesudas et al. | 73/61.46 |
| 5,698,979 | A | | 12/1997 | Taicher et al. | 324/303 |
| 5,936,405 | A | * | 8/1999 | Prammer et al. | 324/303 |
| 6,111,408 | A | * | 8/2000 | Blades et al. | 324/303 |
| 6,346,813 | B1 | | 2/2002 | Kleinberg | 324/303 |

OTHER PUBLICATIONS

NMR Spectroscopy, Organic Chemistry OnLine, http://chipo.chem.uic.edu/web1/ocol/spec/C13–I.htm pp. 1–3.
Arthur Park et al.; *Improved Oil Saturation Data Using Sponge Core Barrel*, SPE 11550, 1983 Production Operation Symposium, Feb. 27–Mar. 1, 1983, pp. 87–91, 10 Figs.
C. Westbrook and C. Kaut "MRI In Practice" Second Edition Blacwell Science Ltd. p. 224, Jan. 1998.*

* cited by examiner

*Primary Examiner*—Diego Gutierrez
*Assistant Examiner*—Tiffany A. Fetzner
(74) *Attorney, Agent, or Firm*—Madan, Mossman & Sriram, P.C.

(57) ABSTRACT

A method for characterizing a fluid sample withdrawn from an earth formation. The method includes performing nuclear magnetic resonant spin echo measurements on the fluid sample at a nuclear magnetic resonant frequency of carbon-13. Amplitudes of the spin echo measurements are summed. The summed measurements are spectrally analyzed. The fluid is characterized by determining whether aromatic hydrocarbons are present by measuring an amplitude of the spectrally analyzed spin echo measurements at about 130 part per million shift from the carbon-13 frequency. The fluid is also characterized by determining whether aliphatic hydrocarbons are present by measuring an amplitude of the spectrally analyzed spin echo measurements at about 30 parts per million frequency shift.

31 Claims, 6 Drawing Sheets

Prior Art Fig. 1

NUCLEAR MAGNETIC RESONANCE FLUID CHARACTERIZATION APPARATUS AND METHOD FOR USING WITH ELECTRIC WIRELINE FORMATION TESTING INSTRUMENTS

Matter enclosed in heavy brackets [ ] appears in the original patent but forms no part of this reissue specification; matter printed in italics indicates the additions made by reissue.

*CROSS-REFERENCES TO RELATED APPLICATIONS*

*This application is a reissue application of U.S. Pat. No. 6,111,409 issued on Aug. 29, 2000.*

BACKGROUND OF THE INVENTION

1. Field of the Invention

The invention is related to the field of electric wireline formation fluid testing instruments, and to apparatus and methods for characterizing samples of connate fluids withdrawn from earth formation by such formation fluid testing instruments.

2. Description of the Related Art

Electric wireline formation fluid testing instruments are used to withdraw samples of connate fluids from earth formations penetrated by a wellbore. Certain characteristics of the fluid samples can be used to infer the nature of the connate fluids in the formations, particularly whether the fluid samples include petroleum, and the physical properties of the petroleum if it is present in the fluid samples. Formation testing instruments typically include one or more sample tanks to transport some of the connate fluid to the earth's surface where the sample may be characterized in a laboratory. See for example, U.S. Pat. No. 5,473,939 issued to Leder et al which describes one such formation fluid testing instrument.

A particular difficulty associated with fluid sampling using electric wireline instruments known in the art has been determining the extent to which the fluid samples placed in the tank contain connate fluids from the earth formation, and the extent to which the samples contain the liquid phase ("mud filtrate") of a fluid ("drilling mud") used to drill the wellbore. The mud filtrate enters ("invades") the pore spaces of the earth formation proximal to the wellbore due to hydrostatic pressure and therefore frequently contaminates samples of fluid withdrawn from the formation.

Wireline formation testing instruments known in the art include various apparatus to overcome this limitation. Generally, the formation testing instruments include a means for withdrawing fluid from the formation and selectively discharging the fluid to the wellbore, rather than to the sample tanks, until it is determined that the fluid being withdrawn consists substantially of connate fluid. See the Leder et al '939 patent, for example, which describes a so-called "pump-through" capability. While withdrawing the fluid from the formation and pumping the fluid through the instrument, one or more properties of the fluid can be monitored. The point at which the nature of the withdrawn fluid changes from mud filtrate to connate fluid can generally be inferred from changes in the properties being monitored. The monitored properties include dielectric constant and electrical resistivity. For example, U.S. Pat. No. 5,677,631 issued to Reittinger et al describes a waveguide which enables making measurements related to the electrical conductivity and/or dielectric constant of the fluid being withdrawn. If water forms the liquid phase of the drilling mud, changes in the conductivity and/or dielectric constant can be related to changes in the nature of the withdrawn fluid. Using conductivity and/or dielectric constant to characterize the fluid being withdrawn from the formation has several limitations. First, the liquid phase of the drilling mud may be hydrocarbon-based rather than water-based, making characterization difficult if the connate fluid includes oil. Second, the connate fluid may contain substantially no hydrocarbons and may have an electrical conductivity very nearly the same as that of the mud filtrate, making determination of the nature of the fluid sample difficult. Finally, if the fluid sample contains both hydrocarbons and water, measuring electrical conductivity and/or dielectric constant in a relatively small volume waveguide, as is necessary within the confines of a typical electric wireline formation testing instrument, can result in noisy and unstable measurements, making accurate fluid characterization difficult.

Other methods for characterizing fluid samples include determining various relationships between the pressure and the volume of the fluid sample, such as described in U.S. Pat. No. 5,635,631 issued to Yesudas et al. A limitation to using the method described in the Yesudas et al '631 patent is that withdrawing the fluid from the formation must necessarily be stopped while the pressure/volume relationship of the fluid sample is carefully determined. Using this method to determine the point at which the fluid sample consists of connate fluid would therefore be impracticable because of the amount of time needed. Further, if the connate fluid were to consist mainly of water, the method in the Yesudas et al '631 would not readily indicate whether the fluid sample contained mud filtrate, connate fluid or any combination thereof.

Near infrared ("NIR") photospectroscopy has also been used to characterize the fluid being withdrawn from the earth formation. U.S. Pat. No. 4,994,671 issued to Safinya et al describes a system for NIR photospectroscopy of fluid samples to determine their nature. It has proven difficult in practice to maintain the quality of optics necessary to reliably perform NIR photspectroscopy in a wireline formation testing instrument, primarily because of the opacity of typical crude oils. Further, photospectroscopic methods are generally unable to determine the nature of the fluid sample if the fluid sample and the mud filtrate are both water-based.

Carbon-13 nuclear magnetic resonance ("NMR") spectroscopy is used to determine the chemical structure of carbon containing compounds. Carbon-13 NMR spectroscopy measures frequency shifts in the nuclear magnetic resonant frequency of carbon-13 resulting from combination of carbon atoms in chemical compounds having specific structures. Determining chemical structures of carbon compounds using NMR spectroscopy requires an NMR spectrometer having a resolution of about 1 part per million. This degree of resolution would require an instrument structure having a static magnetic field which is more homogeneous than would be practical for use in a well logging instrument.

SUMMARY OF THE INVENTION

The invention is a method for characterizing a fluid sample withdrawn from an earth formation. The fluid sample is withdrawn through a probe on an electric wireline formation testing instrument. The method includes performing nuclear magnetic resonance spin echo measurements on the fluid sample at a nuclear magnetic resonant frequency of carbon-13. Amplitudes of the spin echo measurements are summed. The summed measurements are spectrally analyzed. The fluid is characterized by determining whether aromatic hydrocarbons are present by measuring an amplitude of the spectrally analyzed spin echo measurements at about 130 part per million frequency shift from the carbon-13 resonant frequency. The fluid is also characterized by determining whether aliphatic hydrocarbons are present by measuring an amplitude of the spectrally analyzed spin echo measurements at about 30 parts per million frequency shift.

A nuclear magnetic resonance sensor according to the invention includes a permanent magnet for inducing a substantially homogeneous static magnetic field in at least a portion of the fluid sample, and a first antenna for inducing a radio frequency magnetic field in the fluid sample. The radio frequency magnetic field is substantially perpendicular to a magnetization direction of the static magnetic field. Circuits are coupled to the antenna for performing nuclear magnetic resonance spin echo measurements at a nuclear magnetic resonant frequency of carbon-13. The circuits include means for stacking the spin echo measurements over a measurement sequence. The apparatus includes a spectral analyzer for measuring amplitudes of components of the spin echo measurements at frequency shifts of 30 and 130 parts per million from the carbon-13 resonant frequency. A preferred embodiment includes shim coils proximal to the fluid sample. A controllable DC source is connected to the shim coils. The output of the DC source is adjusted in response to the output of a Hall sensor or the like to maintain a substantially constant static magnetic field amplitude in the fluid sample even while the permanent magnet field strength changes with temperature. The entire sensor assembly including the permanent magnet, shim coils and antennas can be included in fluid flow lines in an electric wireline formation testing instrument.

BRIEF DESCRIPTION OF THE DRAWINGS

*FIGS. 7A–7C* show representative analyses for connate water, aromatic-based mud filtrate and aliphatic-containing crude oil, using the method of the invention.

DESCRIPTION OF THE PREFERRED EMBODIMENT

The invention is a nuclear magnetic resonance sensor disposed in an electric wireline instrument for withdrawing fluid samples from earth formations penetrated by a wellbore. One such instrument for withdrawing fluid samples is described, for example, in U.S. Pat. No. 5,635,631 issued to Yesudas et al. A feature of the instrument described in the Yesudas et al '631 patent which is particularly useful with this invention is a so-called "pump-through" capability. An electric wireline formation testing instrument having pump-through capability can withdraw fluid from the earth formation and selectively discharge the withdrawn fluid into the wellbore until which time as it has been determined that the fluid being withdrawn from the earth formation consists substantially of connate fluid, rather than the liquid phase of the drilling mud ("mud filtrate"). When the fluid being withdrawn is determined to consist substantially of connate fluid, the fluid being withdrawn can then be selectively redirected into one or more sample tanks for transportation of a predetermined volume of the fluid to the earth's surface. It should be noted that pump-through capability is not necessary for this invention, however having pump-through capability makes it more likely to be able to direct a substantially uncontaminated sample of connate fluid into the one or more sample tanks.

Figure 1:
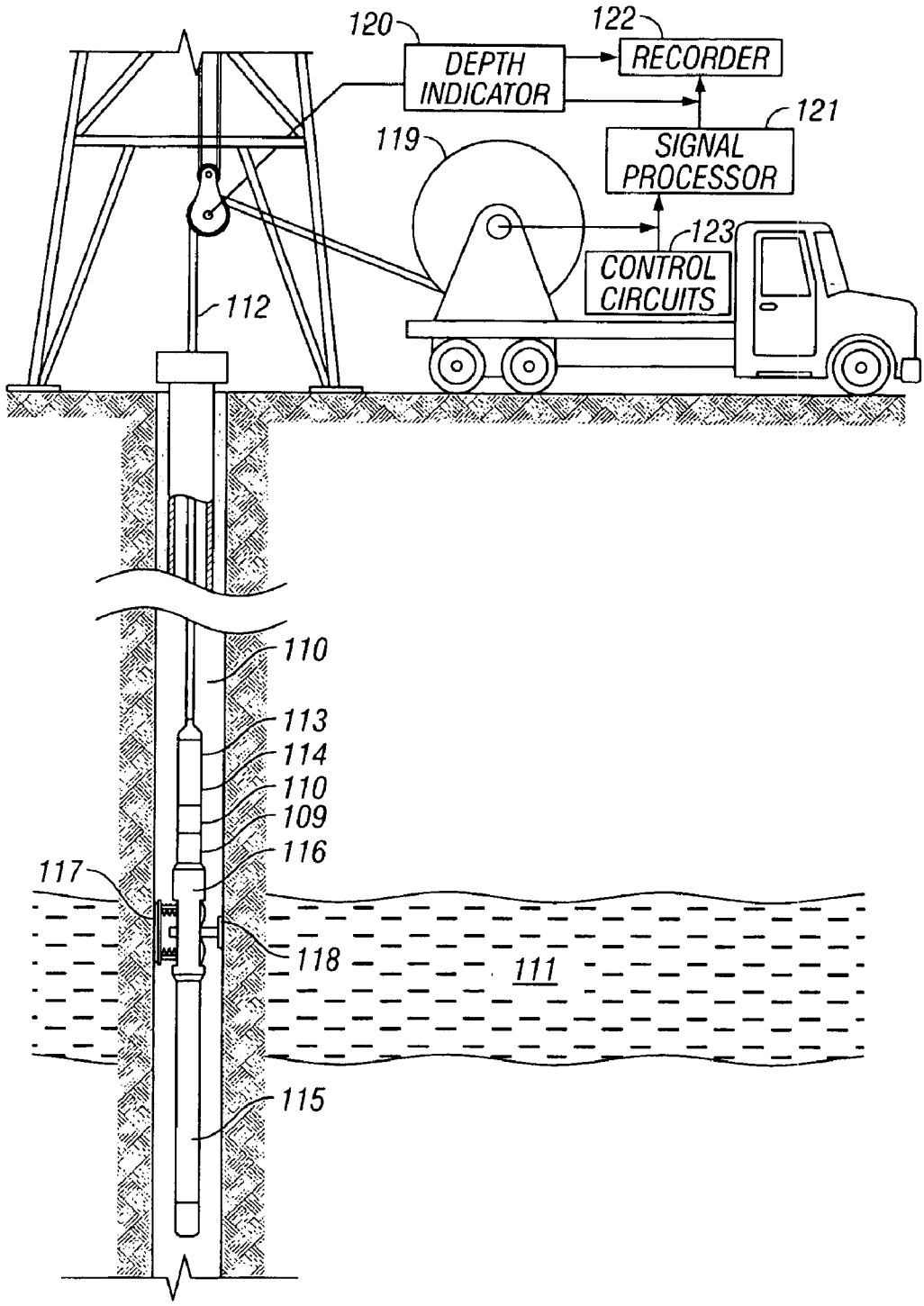
FIG. 1 (*Prior Art*) shows an electric wireline formation testing instrument in a wellbore deployed for withdrawing a sample of fluid from an earth formation.

The electric wireline formation test tool is generally shown in FIG. 1 at 113. The tool 113 is attached to one end of an armored electrical cable 112 and is lowered into a wellbore 110 drilled through the earth. The cable 112 can be extended into the wellbore 110 by means of a winch 119 located at the earth's surface.

The tool 113 comprises a back-up shoe and a mechanism for laterally extending the shoe, as shown generally at 117, both of which are disposed within a housing 116. The housing 116 also contains a tubular probe 118 which can be selectively extended and put into contact with the wall of the wellbore 110. A sample tank 115 can be attached to the lower end of the housing 116 and can be selectively hydraulically connected to the probe 118 in order to store samples of fluids withdrawn from the earth. The probe 118, the back-up shoe 117 and selective valves (not shown) disposed within the housing 116 for operating the probe 118 and the shoe 117 can be of types familiar to those skilled in the art, and can receive hydraulic operating power from an hydraulic power unit 109 attached to the upper end of the housing 116. A nuclear magnetic resonance sensor 10 can be included in the instrument 113 for measuring characteristics of fluids withdrawn from the earth. The sensor 10 will be explained in more detail.

The various operating functions of the tool 113, including extension of the shoe 117 and extension of the probe 118, can be controlled by the system operator entering command signals into control circuits 123 which are located at the earth's surface and are electrically connected to the cable 112, as is understood by those skilled in the art. The command signals can be decoded in an electronics unit 114 disposed within the housing 116. As will be further explained, the tool 113 comprises sensors (not shown in FIG. 1) for measuring nuclear magnetic resonance properties, pressure and volume within hydraulic lines (not shown in FIG. 1) connected to a sample chamber (not shown in FIG. 1). Measurements made by the sensors (not shown) are transmitted to the earth's surface as electrical signals generated by the electronics unit 114. At the earth's surface the signals are decoded by a signal processor 121 which is also electrically connected to the cable 112. The decoded signals are reformatted into measurements which can be observed by the system operator and can be recorded by a recorder 122 connected to the signal processor 121.

As the tool 113 is lowered into the wellbore 110, the depth at which the tool is located is indicated by a depth indicator 120 which is in contact with the cable 112 and measures the amount of cable 112 extended into the wellbore 110. When the tool 113 is positioned adjacent to a formation of interest, shown generally at 111, the system operator enters commands into the control circuits 123 to lock the tool 113 in position by extending the back-up shoe 117. The probe 118 is then extended, and withdrawal of a fluid sample can be initiated.

Figure 2:
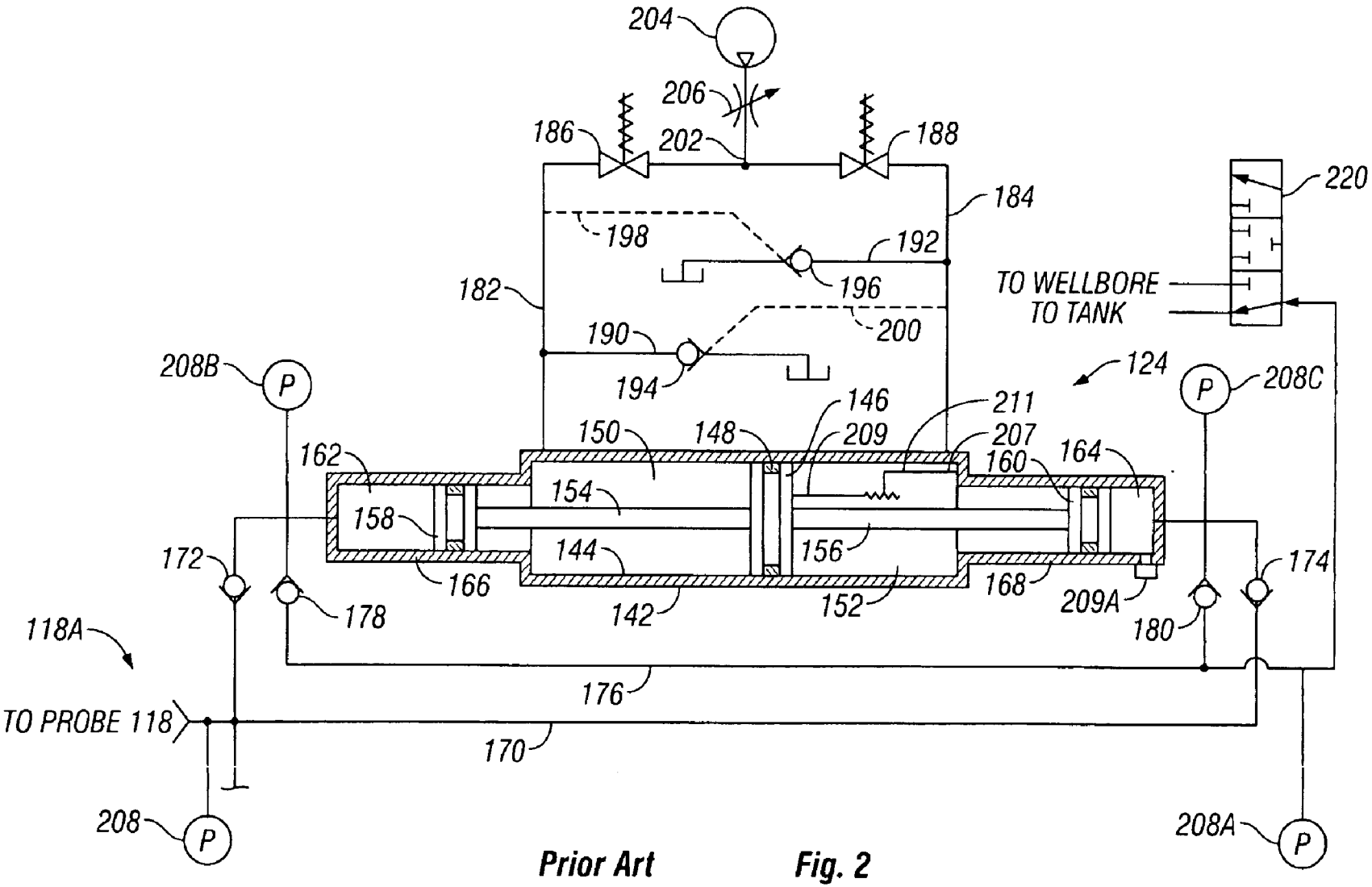
Fig. 2 Prior Art
FIG. 2 (*Prior Art*) shows hydraulic controls and a fluid pump from the testing instrument shown in FIG. 1.

The means by which a fluid sample can be withdrawn from the formation of interest (111 in FIG. 1) can be better understood by referring to FIG. 2. A bidirectional, hydraulically powered pump, shown generally at 124, can controllably withdraw fluids through the probe (118 in FIG. 1). If so desired by the system operator, the pump 124 can further be used to discharge the fluids either into the sample tank (115 in FIG. 1) or into the wellbore (110 in FIG. 1).

The pump 124 comprises a drive cylinder 144, inside which is located at drive piston 146. The drive piston 146 is sealed against the inner wall of the drive cylinder 144 by an o-ring 148 or similar sealing device. The drive piston 146 is connected on one side to a first drive link 154, and on the other side is connected to a second drive link 156. The first drive link 154 is connected to one side of a first pumping piston 158. The second drive link 156 is similarly connected to a second pumping piston 160 disposed on the opposite side of the drive piston 146 to the first pumping piston 158. The first 158 and the second 160 pumping pistons are each respectively positioned within first 166 and second 168 pump cylinders disposed on opposite ends of the drive cylinder 144. Axial motion of the drive piston 146 is translated into equivalent axial motion of both the first 158 and second 160 pumping pistons.

The drive piston 146 is moved axially by selective application of hydraulic pressure to either one side or to the other side of the drive piston 146. Hydraulic pressure is provided by an hydraulic pump 204 which is disposed in the hydraulic power unit (shown in FIG. 1 as 109). The hydraulic pump 204 is connected to a controllable pressure regulator 206 which provides the hydraulic pressure to move the drive piston 146. The discharge pressure from the regulator 206 can be controlled by the system operator entering appropriate commands into the control circuits (shown in FIG. 1 as 123). The controllable regulator discharge provides the system operator with a substantial degree of control over the rate at which the drive piston 146 moves since the drive piston 146 must overcome forces of fluid pressures acting on the pumping pistons 158, 160 in order to move.

The discharge from the regulator 206 is provided to hydraulic lines 202. The lines 202 connect to a first 186 and to a second 188 selective hydraulic valve. The selective valves 186, 188 can be operated by control signals sent from the control circuits (shown as 123 in FIG. 1) and decoded in the electronics unit (shown at 114 in FIG. 1). The control signals provide operation of the valves 186, 188 in accordance with the pump 124 function selected by the system operator by entering appropriate commands into the control circuits 123.

When the first valve 186 is opened, hydraulic pressure is applied through a first hydraulic control line 182 to a first chamber 150 in the drive cylinder 144, which is bounded at one end by the drive piston 146 and at the other end by the first pumping piston 158. The diameters of the first pump cylinder 166, and therefore, the first pumping piston 158 (and consequently their cross-sectional areas) are smaller than the diameter (and cross-sectional area) of the drive piston 146. Hydraulic pressure within the first drive chamber 150 therefore exerts more force on the drive piston 146 than on the first pumping piston 158, which causes motion of the drive piston 146, and all the previously described components that are attached to it, in the direction of the second pump cylinder 168. Hydraulic oil (not shown) is also present in a second drive chamber 152 disposed on the opposite side of the drive piston 146 and axially bounded by the drive piston 146 on one end and the second pumping piston 160 on the other end. As the drive piston 146 moves toward the second pump cylinder 168, the hydraulic oil in the second drive chamber 152 is displaced through a second hydraulic line 184 into a second discharge line 192 connected to a hydraulic oil supply tank (not shown) through a pilot operated check valve 196. The check valve 196 is held open by the operating hydraulic pressure from the line 202 applied through a control line 198 connected to the first hydraulic line 182. A similar, oppositely connected check valve, shown at 194, is connected through a control line 200 to the second hydraulic line 184 and vents the first hydraulic line 182 to the supply tank (not shown) when the drive piston 146 is moved in the opposite direction.

Motion of the drive piston 146 can be reversed by closing the first valve 186 and opening the second valve 188, thereby applying hydraulic pressure through the second hydraulic line 184 to the second drive chamber 152. The operation of the two valves 186, 188 can be performed automatically if the system operator instructs the control circuits 123 to operate the pump 124 continuously. The second pumping piston 160 can be substantially the same diameter as the first pumping piston 158, and thereby be smaller in diameter than the drive piston 146. Therefore hydraulic pressure applied to the second drive chamber 152 will cause motion of the drive piston 146 towards the first pump cylinder 166. As previously explained, the pressure on the second line 184 is also conducted through the control line 200 to open the pilot operated check valve at 194, which enables venting of the first drive chamber 150 to the supply tank (not shown).

Axial motion of the drive piston 146, which as previously explained is translated into equivalent axial motion of the first 158 and second 160 pumping pistons, results in corresponding changes in volume of a first 162 and of a second 164 pump chamber. The pump chambers 162, 164 can be selectively hydraulically connected to the probe 118 in order to withdraw fluid from the formation (111 in FIG. 1).

A particular feature of the pump 124 which enables direct determination of the volume of the first 162 and the second 164 pump chambers is a displacement sensor, which in the present embodiment can be a linear potentiometer 211 disposed inside the drive cylinder 144 and connected by a link 209 to the drive piston 146. Axial motion of the drive piston 146 results in directly corresponding change in the resistance of the potentiometer 211 as applied to a signal line 207. The resistance as applied to the signal line 207 is converted into a corresponding signal in the electronics unit (shown in FIG. 1 as 114), which signal can be decoded in the signal processor (shown as 121 in FIG. 1) and converted into a measurement of the position of the drive piston 146, and thereby the exact volume of either pump chamber 162, 164, since the axial motion of all three pistons 146, 158, 160 is equivalent. It is contemplated that other means for measuring the axial position (and thereby the volume of the pumping chambers 162, 164) of the drive piston 146 or of the first 158 or second 160 piston can be employed, for example an acoustic travel time sensor disposed within either drive chamber 150 or 152.

When withdrawal of a sample from the formation (shown at 111 in FIG. 1) is begun, the drive piston 146 is typically positioned so that either the first 158 or the second 160 pumping piston is fully extended into its respective pumping chamber 162 or 164. Withdrawal of a sample is begun by application of hydraulic pressure to the appropriate drive chamber 150 or 152 (adjacent to the completely compressed pump chamber into which its pump piston 158 or 160 is fully extended), whereupon the drive piston 146 moves and correspondingly displaces the pumping pistons 158, 160, thereby increasing the volume of the fully compressed pumping chamber 162 or 164.

The first 162 and second 164 pumping chambers are connected, respectively to a first 172 and a second 174 inlet check valve, both of which enable flow from the probe (shown as 18 in FIG. 1) into an inlet flowline 170 (connected as shown at 118A to the probe 118) on the expansion stoke of the respective pumping chamber 162 or 164. The inlet flowline 170 can also be connected to a highly precise pressure transducer 208 (the signal output of which is connected to the electronics unit 114) which enables substantially continuous measurement of the pressure in the flowline 170. A nuclear magnetic resonance sensor (not shown in FIG. 2) can be included in the inlet flowline 170 between the probe 118 and the probe inlet 118A to enable fluid withdrawn from the formation (111 in FIG. 1) to be analyzed.

During the discharge stroke on one chamber 162 or 164, corresponding to an expansion stroke in the opposing chamber 164 or 162, discharge from the compressing chamber 162 or 164 is conducted, respectively, through a first 178 and second 180 discharge check valve into a discharge line 176. The discharge line 176 can be selectively hydraulically connected to the sample tank (shown in FIG. 1 as 115), vented to the wellbore (shown in FIG. 1 as 110), or the discharge line 176 can be hydraulically closed at its end. Selective connection of the discharge line 176 can be performed by a four-way solenoid operated valve as shown at 220. The solenoid can operate in response to commands entered into the control circuits (123 in FIG. 1) by the system operator.

The invention provides, among other things, a means for determining the nature of the fluid being withdrawn from the formation, particularly whether the fluid consists partially or entirely of mud filtrate. The invention uses nuclear magnetic resonance (NMR) spectroscopy to determine the presence and the general type of hydrocarbon compounds in the fluid being withdrawn from the formation.

It is to be clearly understood that the formation testing instrument shown in FIG. 1 including the pump and hydraulic controls shown in FIG. 2 is only one example of a formation testing instrument which can use the sensor (10 in FIG. 1) according to this invention. It is only necessary for any such testing instrument used with the sensor of the invention to provide some means for withdrawing fluid from the earth formations and moving the fluid into the sensor 10 for analysis. Accordingly, the particular structures of the instrument, pump and hydraulic systems as shown in FIGS. 1 and 2 are not meant to limit the invention.

Figure 3:
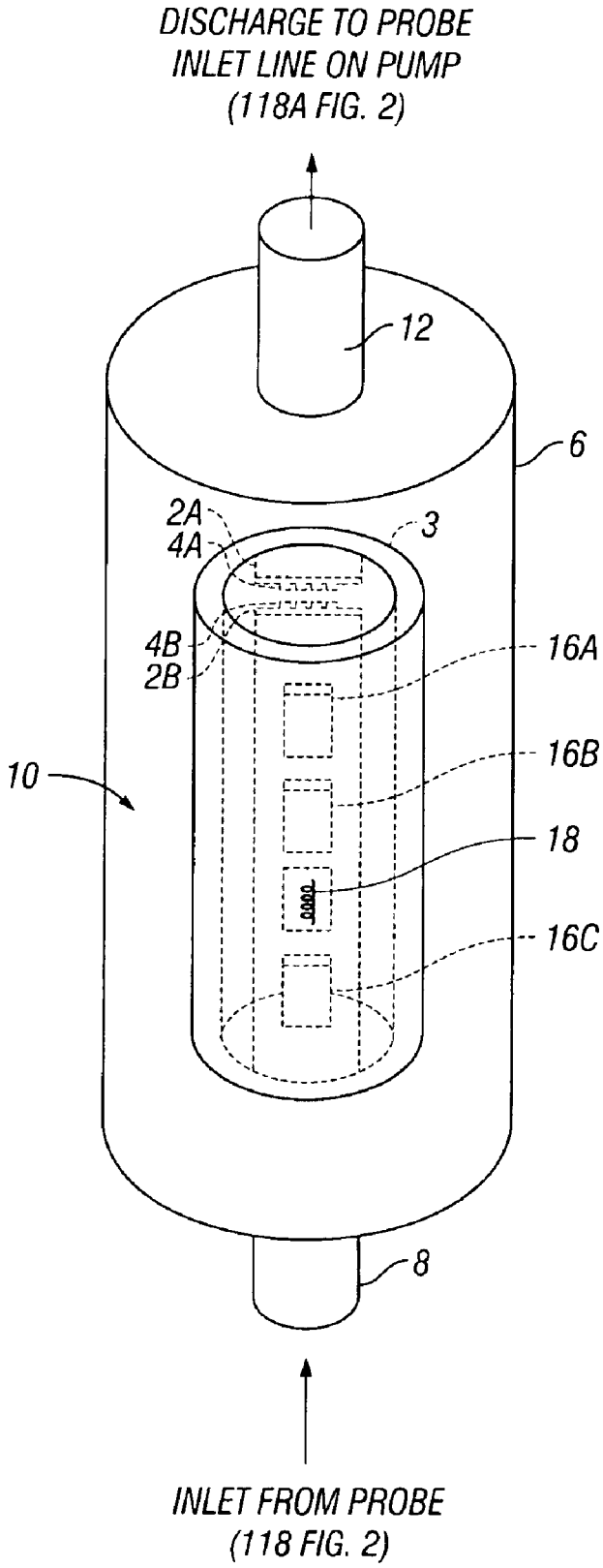
FIG. 3 shows a nuclear magnetic resonance (NMR) sensor according to the invention disposed in an hydraulic isolation chamber.

Referring now to FIG. 3, the nuclear magnetic resonance ("NMR") sensor 10 can be disposed at any convenient location along an hydraulic line, such as the inlet flowline (170 in FIG. 2) connecting the probe (118 in FIG. 1) and the inlet side of the pump (124 in FIG. 2). As fluid is withdrawn from the earth formation (111 in FIG. 1) through the probe (118 of FIG. 1) it enters the sensor 10 through a fluid inlet 8 in a pressure-sealed chamber 6. The pressure-sealed chamber 6 can be disposed in a convenient location in the instrument housing (113 in FIG. 1) to hydraulically isolate the fluid withdrawn from the earth formation (111 in FIG. 1). After NMR measurements are performed on the fluid in the chamber 6, continued operation of the pump (124 in FIG. 2) can cause the fluid to be moved through a fluid discharge 12 in the chamber 6 into the pump (124 in FIG. 2) for eventual disposal either into the wellbore or into a sample tank (not shown) as is explained in the Yesudas et al '631 patent. It should be noted that the sensor 10 can also be located in the pump discharge line if it is convenient for the system designer.

The sensor 10 can include permanent magnets 2A, 2B preferably made from Samarium-Cobalt or similar magnetic material having remanence magnetization which is relatively stable with respect to temperature. In this embodiment of the invention, the magnets 2A, 2B can be surrounded by a substantially cylindrical flux closure or "yoke" 3. Each magnet 2A, 2B can have its own pole piece 4A, 4B on the respective face of each magnet directed towards the center of the sensor 10. The magnets 2A, 2B, yoke 3, and pole pieces 4A, 4B provide a substantially homogeneous static magnetic field in the center of the sensor 10 having a magnitude of about 5,708 Gauss. The direction of magnetization of the magnets 2A, 2B is substantially perpendicular to the longitudinal axis of the sensor 10. Three radio frequency antenna 16A, 16B, 16C are disposed along the axis of the sensor 10 in between the magnets 2A, 2B. The antennas 16A, 16B, 16C as will be further explained, are used for sequential NMR experiments on the fluid in the center of the sensor 10. The sensor 10 can include a Hall probe 18 or similar device for measuring the magnitude of the static magnetic field induced by the magnets 2A, 2B so that the magnitude of the field can be adjusted for changes in the strength of the 2A, 2B magnets with temperature, as will be further explained.

Figure 4:
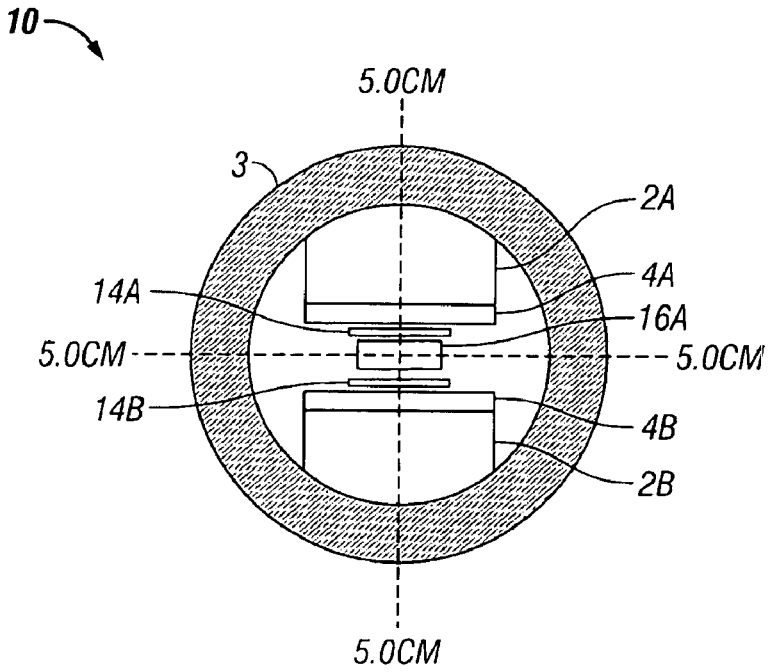
FIG. 4 shows an end view of the NMR sensor of the invention detailing the location of permanent magnets and antennas.

The structure of the sensor 10 can be better understood by referring to an end view in FIG. 4. The magnets 2A, 2B are each polarized as shown by an arrow thereon, generally perpendicular to the longitudinal axis of the sensor 10. The axial length of the sensor 10 should be much longer than the diameter of the region in the center of the sensor 10 having substantially homogeneous static magnetic field, so that NMR experiments can be performed in different locations along the length of the sensor by each of the three antennas (16A, 16B, 16C in FIG. 3) as will be further explained. Pole pieces 4A, 4B can be made of a high magnetic permeability material such as soft iron or the like and can be attached to inner face of each magnet 2A, 2B. The cylindrical yoke 3 can contact each magnet 2A, 2B on the face opposite the location of the pole pieces 4A, 4B. The yoke 3 can be made from a high magnetic permeability material similar to that used for the pole pieces 4A, 4B. The combination of yoke 3, pole pieces 4A, 4B and the magnets 2A, 2B provides a substantially homogeneous static magnetic between the magnets 2A, 2B, the field polarized in the same direction as the polarization direction of the magnets 2A, 2B. Shim coils 14A, 14B can be located in between the magnets 2A, 2B. The shim coils, as will be further explained, can be connected to a controllable direct current (DC) power source to provide a supplemental static magnetic field for compensating changes in the magnetic field strength resulting from changes in ambient temperature. The location of the RF antennas with respect to the magnets 2A, 2B and shim coils 14A, 14B is shown generally at the uppermost antenna 16A. The antennas (16A, 16B, 16C in FIG. 3) can be wire coils wound so that the RF magnetic field induced by the antennas is substantially parallel to the longitudinal axis of the sensor 10. This direction is also perpendicular to the direction of the static magnetic field and is therefore suitable for performing NMR experiments. The arrangement shown in FIGS. 3 and 4 is only an example of arrangements of permanent magnet and antennas which have the requisite properties for conducting NMR experiments in a fluid sample. Other arrangements of permanent magnet and antenna are possible, so the arrangement shown in FIG. 3 is not to be construed as a limitation on the invention. The principle requirements for magnets and antennas is that the magnet induce a substantially homogeneous magnetic field in the location of the fluid to be analyzed, and that the antenna induce an RF magnetic field which is also substantially homogeneous and perpendicular to the static magnetic field in the location of the fluid to be analyzed.

The arrangement of magnets, yokes and antennas shown in FIGS. 3 and 4 provides a substantially homogeneous static magnetic field in a cylindrical volume in the center of the sensor 10. If the cylindrical yoke 3 has an external diameter of about 6 cm as shown in FIG. 4, the homogeneous static magnetic field will exist within a cylindrical volume of about 1 cm in diameter.

Figure 5:
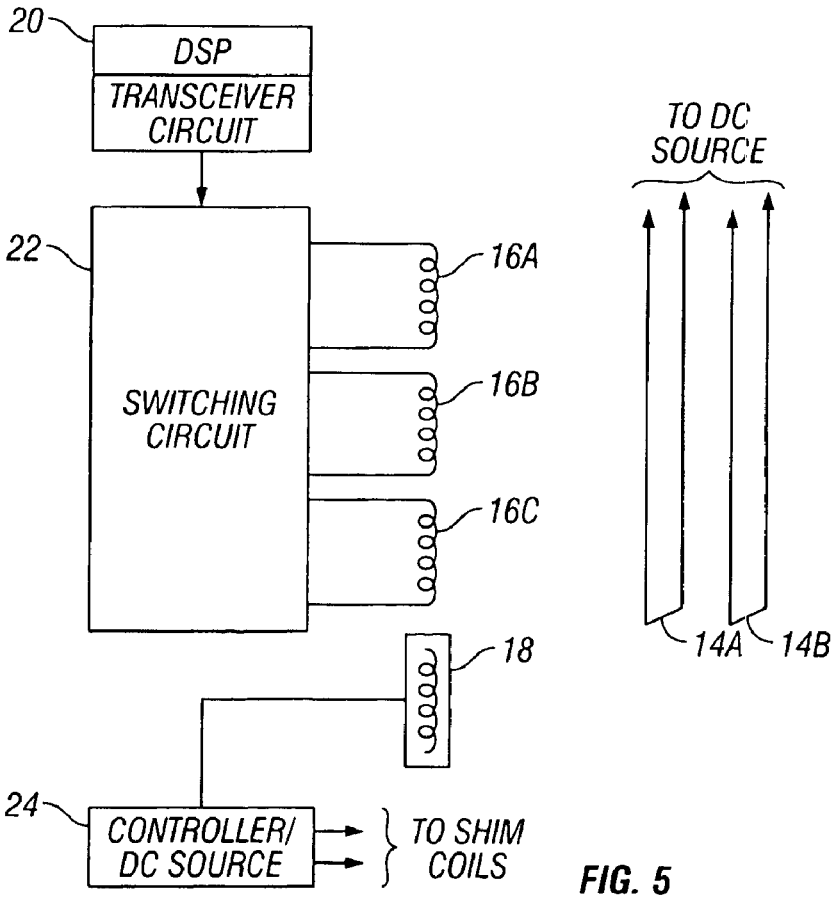
FIG. 5 shows a functional block diagram of circuits used to make NMR spectroscopy measurements using the NMR sensor of the invention.

Operation of the sensor 10 can be better understood by referring to FIG. 5. The antennas 16A, 16B, 16C can be connected to a transceiver circuit 20 through a switching circuit 22. The transceiver circuit 20 generally can include a radio frequency power source which generates controlled-duration pulses or RF power, and switching circuits for selectively connecting the selected antenna (16A, 16B or 16C) between the RF source and a receiver circuit (not shown separately). The receiver circuit is for detecting voltages induced in the selected antenna by nuclear magnetic resonance. Circuits suitable for the transceiver 20 are described, for example, in U.S. Pat. No. 5,712,566 issued to Taicher et al. The transceiver 20 also can include digital signal processing ("DSP") circuits for performing certain calculations on the measurements which will be further explained.

Irrespective of the magnetic material from which they are made, the magnets (2A, 2B in FIG. 4) will to some degree have remanence magnetization which is affected by the ambient temperature around the magnets. It is not at all unusual for well logging instruments to be subjected to a temperature range from 0 to 200° C. Since the NMR experiments performed by the sensor (10 in FIG. 3) are intended to be made in a homogeneous static magnetic field, the sensor 10 includes so-called "shim" coils 14A, 14B which selectively induce a magnetic field superimposed on the static magnetic field induced by the magnets (2A, 2B in FIG. 3). The intensity of the total static field can be measured by the Hall probe 18 or similar device, which can be connected to a control circuit 24. The control circuit 24 applies a direct current the shim coils 14A, 14B, the magnitude of which is related to the output of the Hall probe 18, so that the total magnitude of the static magnetic field in between the magnets 2A, 2B can be maintained substantially constant. As is understood by those skilled in the art, the magnetic resonant frequency of selectively RF-excited nuclei will depend on the magnitude of the static magnetic field in which they are polarized. By maintaining a substantially constant static magnetic field magnitude, the need to adjust the frequency of the RF magnetic field for NMR experimentation can be reduced or eliminated. The shim coils 14A, 14B and source 24 should be able to provide about 100 Gauss superimposed field magnitude to be able compensate the static magnetic field for changes in remanence magnetization of the magnets (2A, 2B in FIG. 3). The amount of static field amplitude required to be provided by the shim coils 14A, 14B will depend on the type of magnet material used for the magnets. Thermally more stable magnet materials such as Samarium Cobalt will require smaller field adjustment using the shim coils 14A, 14B than other magnet materials such as ferrite.

The invention is designed to identify the nature of the fluid disposed in the sensor 10 by carbon-13 NMR spectroscopy. As described in the Background section herein, laboratory carbon-13 NMR spectroscopy measurements require an instrument resolution of 1 part per million (ppm) to determine chemical structures of carbon compounds. This degree of resolution would make impracticable the construction of an NMR spectrometer for use in a wireline formation fluid testing instrument. It has been determined, however, that a resolution of about 50 ppm can be adequate to determine the relative presences of aliphatic and aromatic carbon compounds in the a fluid sample. Aliphatic and aromatic compounds are almost always present in crude petroleum, and aromatic compounds are commonly used in the liquid phase of oil based drilling fluids. Therefore determination of the presence of one or both of these types of carbon compounds can be used to characterize the fluid sample. The magnet structure shown in FIG. 4 can provide a static magnetic field having a homogeneity of 50 ppm or better.

Using the suggested static magnetic field magnitude of 5,708 Gauss, carbon-13 will have a Larmor (NMR resonant) frequency of about 6.12 MHz. At 6.12 MHz, an instrument resolution of 50 ppm would require a receiver bandwidth of about 900 Hz. The transceiver 20, if designed as described in the Taicher et al '566 patent, for example, can be programmed to conduct a Carr-Purcell-Meiboom-Gill (CPMG) pulse/measurement sequence using a radio frequency of about 6.12 MHz. CPMG sequences, as known in the art, include transmission of an initial RF pulse through the antenna (such as 16A in FIG. 3) having a duration which reorients magnetic spin axes of the susceptible nuclei 90° from their orientation along the static magnetic field. The initial 90° RF pulse is followed by a succession of RF pulses each having a duration which reorients the nuclear spins by 180°. Between the 180° pulses, the amplitude is measured of "spin echoes" resulting from rephrasing of nuclear spin axes as they precess around the static magnetic field. The time between 180° pulses is referred to as the interecho spacing.

While the number of 180° pulses and resulting spin echoes in the CPMG sequences is not critical, it is contemplated that adequate signal-to-noise ratio will be obtained if the CPMG sequence extends over a time span approximately equal to the transverse relaxation time of the fluid sample. 500 milliseconds, or about 50 spin echoes using an interecho spacing of 10 milliseconds should provide adequate signal-to-noise. The contemplated time of 10 milliseconds interecho spacing is selected for the expected decay time for each individual spin-echo, as will be further explained.

The transceiver 20 can include an analog-to-digital converter as part of the DSP circuits, as suggested in Taicher et al '566 patent. The amplitude of each spin echo can be measured using a digital sample rate of about 0.55 milliseconds between each sample, which represents a frequency of twice the receiver bandwidth. Each spin echo should be digitized over a time span related to the decay time of the individual echo. This time is known as the free induction decay time, represented by $T_2$*, and is inversely propor tional to the degree of homogeneity of the static magnetic field as shown in the following expression:

$$T_2^* = \frac{1}{2\pi f_0 \Delta} \quad (1)$$

where the homogeneity is represented by Δ. At the 6.12 MHz Larmor frequency for carbon-13 in the static magnetic field of 5,708 Gauss, and a field homogeneity of 50 ppm, the digitization time for each spin echo should be no less than 3.12 milliseconds. therefore no fewer than six digital samples at a rate of 1,800 Hz should be made of each sample. The digital sample rate can be increased as long as the signal is band limited to about 900 Hz (this being the product of the sensor 10 resolution and the Larmor frequency). It should be noted that the required receiver bandwidth and corresponding spin echo sample times depend on the intended sensor resolution and the degree of homogeneity of the static magnetic field, so the figure of 900 Hz bandwidth only applies given the senor 10 construction shown herein and the sensor resolution described herein.

The digitized spin echoes can be formatted in the electronics unit (114 in FIG. 1) into signals for transmission to the signal processor (121 in FIG. 1) for decoding and further processing as will be explained.

To process the digitized spin echoes into characterizing information about the fluid sample, each spin echo in each CPMG sequence can have time correspondent ones of the digitized amplitude measurements summed or averaged over each entire CPMG sequence. The result of the summing is a set of digital amplitude values for each CPMG sequence. In this embodiment of the invention, three antennas 16A, 16B, 16C are provided at different locations along the longitudinal axis of the sensor 10. By including a plurality of antennas each energizing a different volume within the fluid sample, it is possible to acquire NMR signals having improved signal-to-noise in a relatively short time period. The improved signal-to-noise is obtained by summing or "stacking" the spin echoes measured using each antenna 16A, 16B, 16C. The stacking can be performed in the signal processor (121 in FIG. 1). The antennas 16A, 16B, 16C can each be selectively energized for performing an CPMG measurement sequence by using the switching circuit 22. As is known in the art, nuclei which have been transversely polarized by NMR spin echo experimentation gradually "relax" or return to magnetic spin orientation aligned with the static magnetic field. During the longitudinal relaxation, no further experimentation on the particular sample is practical. The nuclei of the fluid samples in the location of the non-energized antennas, however, remain substantially polarized along the static magnetic field and can be subjected to NMR spin-echo experimentation during the longitudinal relaxation period (the "wait time") of the previously transversely polarized (the "experimented on") fluid sample. Spin echo amplitudes measured by each of the antennas 16A, 16B, 16C can also be summed to get spin echo amplitude values having improved signal-to-noise. Using three switched antennas is not a limitation on the invention, but is merely illustrative of the principle of multiple measurements made in different portions of the sample to conserve time. It is contemplated that five or more switched antennas can be used with the sensor 10 of the invention. It is further contemplated that two or more of the antennas can be used to conduct CPMG measurements sequences simultaneously where enough such antennas are used in the particular sensor to enable sufficient wait time between measurement sequences at any single antenna. For example, a measurement cycle for a six antenna system could include measuring CPMG sequences at the first and fourth antennas, next at the second and fifth antennas, and finally at the third and sixth antennas. The cycle can then be repeated at the first and third antennas, and so on for an appropriate number of cycle repetitions to obtain a sufficient signal-to-noise ratio.

Figure 6:
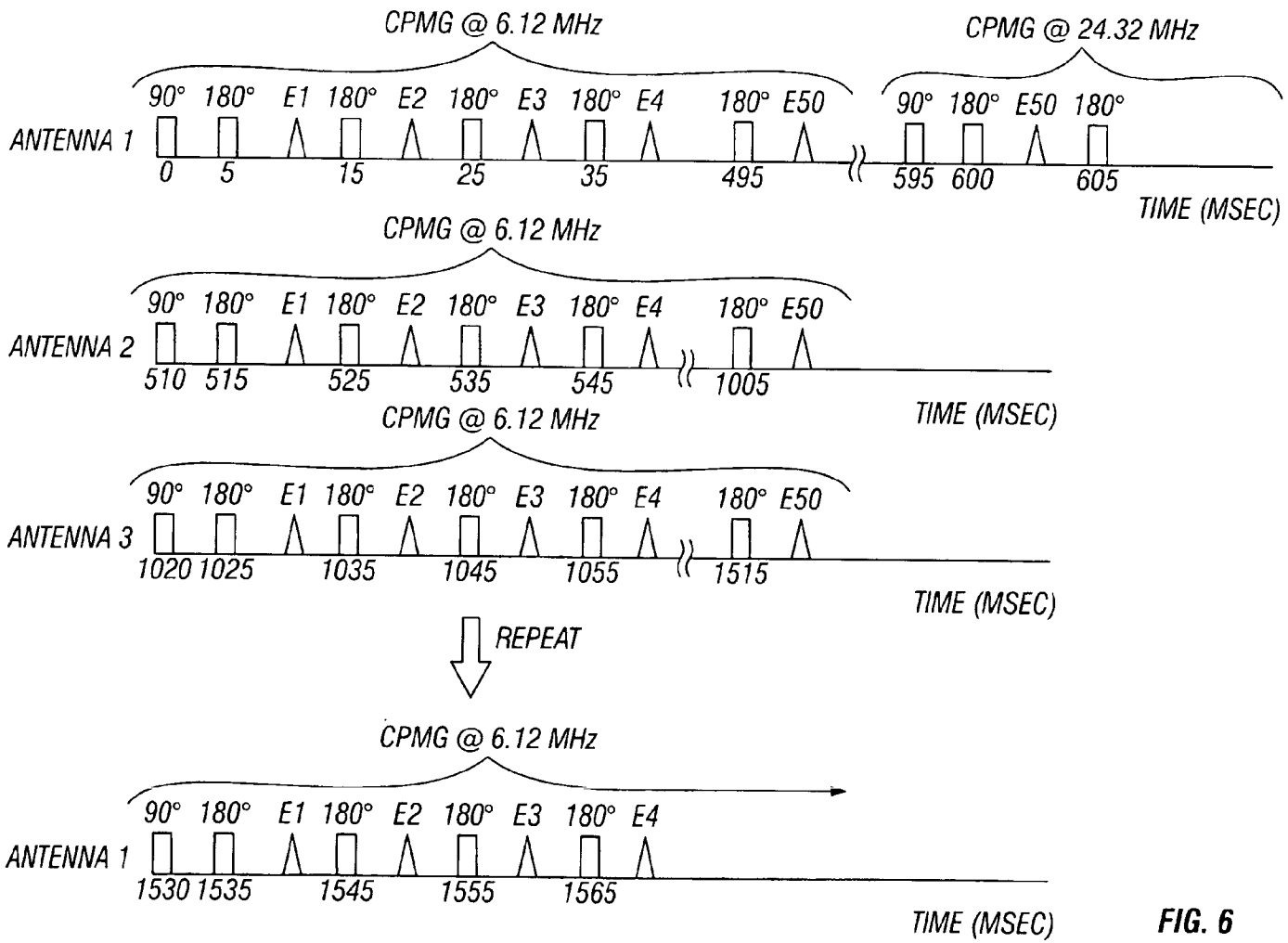
FIG. 6 shows a timing diagram for NMR measurement sequences made using the apparatus of the invention.

A timing diagram showing typical CPMG pulse sequences applied to each of the antennas (16A, 16b, 16C in FIG. 5) is shown in FIG. 6. 90° and 180° pulses at the 6.12 MHz resonant frequency can be applied to the first antenna as shown in the upper timing scale in FIG. 6. Each spin echo occurring after one of the 180° pulses is indicated by E1, E2, E3, and on through E50. Immediately after the end of the CPMG sequence at 6.12 MHz at the first antenna (16A in FIG. 5) a CPMG sequence can be applied to the second antenna (16B in FIG. 5) as shown in the second timing scale in FIG. 6, starting at about 510 milliseconds from the initiation of the sensor operation. As the CPMG sequence is completed at the second antenna, a CPMG sequence can be immediately started at the third antenna (16C in FIG. 5). This entire sequence of CPMG sets at successive antennas can be repeated as shown in the bottom timing scale in FIG. 6, representing a CPMG sequence at 6.12 MHz at the first antennas starting at about 1530 milliseconds from the start of the first such CPMG sequence at the first antenna.

After summing, or "stacking", the spin echo amplitude values from all the CPMG measurement sequences, the resulting stacked spin echo amplitude sample values can then be analyzed using a fast Fourier transform or similar spectral analysis, to generate a Fourier spectrum. The Fourier spectrum will include relative amplitude contributions of different frequency components present in the stacked spin echo amplitude values. The presence or absence of certain frequency components can be used to determine whether aromatic hydrocarbon components and/or aliphatic hydrocarbon compounds are present in the fluid sample. The resolution of the spin echo amplitude measurements in the method of the invention is sufficient to calculate relative amplitudes of signal components at 30 and 130 parts per million (ppm) from the base frequency (the frequency of the RF power used to perform the spin echo measurement sequences.

For example, carbon-13 in xylene generates characteristic spectral peaks in the range of about 130 ppm from the base frequency of 6.12 MHz. Carbon-13 in typical aliphatic (alkane) compounds including $CH_2$ and $CH_3$ molecular groupings therein has characteristic peaks in the 30 ppm range from the base frequency. See, for example, W. Simons, The Sadtler Guide to Carbon-13 Spectra, Sadtler Research Laboratories, 1984. As is known in the art, drilling fluids which include hydrocarbon as the liquid phase typically include aromatic compounds. Crude oils typically include some aliphatic compounds. After performing the Fourier transform on the stacked samples, the amplitude of the spectrum at 130 ppm can be measured, and the amplitude of the spectrum at 30 ppm can be measured. Absence of any substantial spectral amplitude at 130 or 30 ppm indicates that the fluid sample does not include any substantial amount of hydrocarbons, either aromatic or aliphatic type. If the amplitude of the 130 ppm portion of the spectrum shows substantial presence of aromatic hydrocarbons, and the drilling fluid contains such aromatics in the liquid phase, it may be inferred that the fluid sample includes a substantial fraction of mud filtrate. Presence of substantial amounts of aliphatic hydrocarbons, as indicated by substantial amplitude of the 30 ppm portion of the spectrum, indicates that the fluid sample in the sensor 10 includes some connate hydrocarbons. It is therefore possible using the spectroscopy technique of the invention, to discriminate between crude oil, and oil based mud filtrate by determining the relative presence of aliphatic and aromatic compounds in the fluid sample.

Figure 7A:
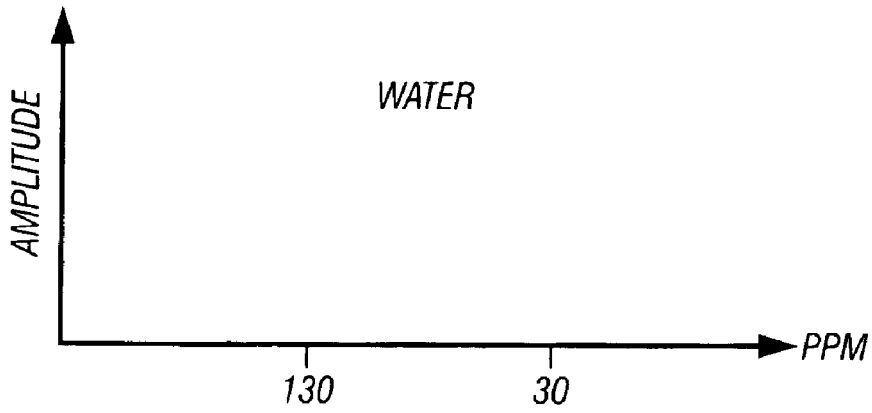
[FIG. 7A–7C]
Figure 7B:
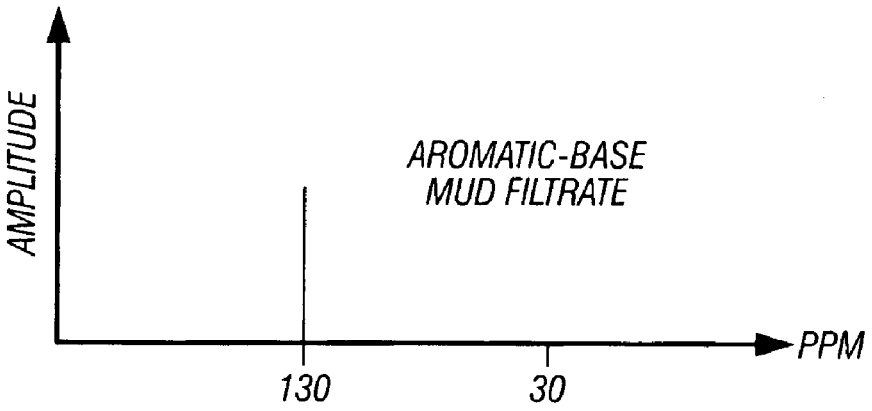
Figure 7C:
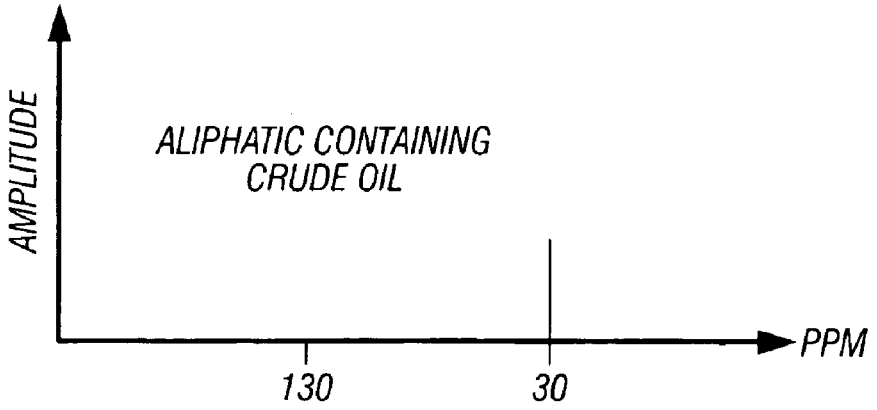

An example of analyses using the method of the invention is shown in graphs in FIGS. 7A–7C. FIG. 7 shows a typical analysis of a fluid sample consisting mainly of water. Neither the 130 ppm portion of the spectrum nor the 30 ppm portion have any appreciable amplitude. In FIG. 7B, the fluid analyzed contains a substantial portion of aromatic hydrocarbon, which can be inferred from the substantial amplitude at 130 ppm and the lack of appreciable amplitude at 30 ppm. This response is typical of oil-based mud filtrates consisting mainly of aromatic compounds. If the mud filtrate consists of aliphatic compounds as well, the analysis of the fluid samples may be improved by first introducing a sample of the mud filtrate to the sensor (10 in FIG. 2) and preforming NMR analysis as described herein. The resulting analysis can be compared to analyses made of fluids withdrawn from the earth formation to determine the extent to which the fluid consists of mud filtrate. An analysis of typical crude oil sample containing both aliphatic compounds and some aromatic compounds is shown in FIG. 7C.

Referring once again to FIG. 6, on the uppermost timing scale showing pulses to be applied to the first antenna (16A in FIG. 5), a series of RF pulses and resulting spin echoes, comprising a CPMG sequence, can be observed past the end of the CPMG sequence at 6.12 MHz. These additional RF pulses can be generated at 24.32 MHZ, which in the 5,708 Gauss static magnetic field of the sensor as described herein represents the NMR frequency of protons (hydrogen nuclei). The CPMG sequence measured at 24.32 MHz can be used to conduct conventional proton relaxometry experiments, for determining properties of the fluid sample such as viscosity. Proton relaxometry methods are known in the art and generally include measurement of the amplitude of each one of the spin echoes to determine the rate of decay of the amplitude. CPMG sequences may be measured successively at the second and third antennas for proton relaxometry during the wait time at the first and second antennas, respectively. Proton relaxometry CPMG sequences made at any one of the antennas after the end of a carbon-13 spectroscopy CPMG sequence will typically not interfere with realignment of the carbon-13 nuclei with the static magnetic field because the radio frequency used for proton relaxometry is substantially different than for carbon-13 spectroscopy. Consequently carbon-13 nuclei will be substantially unaffected by generation of a 24.32 MHz magnetic field. It should also be noted that the sensor (10 in FIG. 3) can include gradient field coils (not shown) connected to a DC power source (not shown) for conducting relaxometry experiments in a gradient magnetic field for the purpose of determining diffusion properties of the fluid sample. Arrangements of gradient coils and methods for conducting such relatometry experiments are known in the art. See for example, U.S. Pat. No. 5,698,979 issued to Taicher et al.

As is known in the art, connate water typically includes some concentration of sodium ions in solution. The concentration of sodium ions is related to the resistivity (conductivity) of the connate water. Using the apparatus of the invention, it is also possible to determine the relative concentration of sodium ions in solution in the fluid sample. the following process steps can be used to determine the relative concentration of sodium in the fluid sample. The antennas 16A, 16B, 16C can be sequentially actuated for measuring CPMG sequences at the resonant frequency of sodium-23, which is about 6.41 MHz. A typical timing sequence for measuring CPMG sequences at each of the three antennas can be observed in FIG. 6. The only substantial difference between the CPMG sequences for carbon-13 and sodium-23 is the frequency of the RF magnetic field. The amplitudes of each spin echo in the CPMG sequences from each of the three antennas can then be summed or stacked. Sodium ions in solution will typically have only a single spectral amplitude peak (a single resonance "line") whose amplitude is related to the relative concentration of sodium in the fluid sample. Therefore the value of the summed spin echo amplitudes will be directly related to the relative concentration of sodium ions in solution.

Those skilled in the art will devise other embodiments of this invention which do not depart from the spirit of the invention as disclosed herein. The invention should therefore be limited in scope only by the attached claims.

What is claimed is:

1. A method for characterizing a fluid sample *in a chamber on a wireline instrument, said fluid* withdrawn from an earth formation, comprising:

performing magnetic resonant spin echo measurements on said fluid sample *in said chamber* at a magnetic resonant frequency of carbon-13;

summing amplitudes of said spin echo measurements;

spectrally analyzing said summed amplitudes;

determining whether aromatic hydrocarbons are present in said fluid sample by measuring an amplitude of said spectrally analyzed summed amplitudes at about 130 parts per million shift from said carbon-13 resonant frequency and determining whether aliphatic hydrocarbons are present in said fluid sample by measuring an amplitude of said spectrally analyzed summed amplitudes at about 30 parts per million frequency shift from said carbon-13 resonant frequency.

2. The method as defined in claim 1 further comprising improving a signal-to-noise ratio of said spin echo measurements by:

performing spin echo measurements on a first portion of said sample *in said chamber* during a wait time between sets of said spin echo measurements performed on a second portion of said sample, said first portion substantially unaffected by a radio frequency magnetic field used to make said spin echo measurements on said second portion; and stacking said spin echo measurements made on said first portion and said second portion.

3. The method as defined in claim 1 further comprising measuring a magnitude of a static magnetic field *in said chamber* used to make said spin echo measurements and superimposing a selectable magnitude magnetic field on said static magnetic field of compensate for temperature induced changes in said magnitude of said static magnetic field.

4. The method as defined in claim 1 further comprising performing nuclear magnetic resonance spin echo amplitude measurements *in said chamber* at a resonant frequency of hydrogen nuclei, and determining a relaxation rate of said hydrogen nuclei.

5. An apparatus [for characterizing] *which characterizes* a fluid sample withdrawn from an earth formation, *said fluid sample being contained in a chamber on a wireline instrument,* comprising:

a magnet [for inducing] *which induces* a substantially homogeneous static magnetic field in at least a portion of said sample *in said chamber*;

a first antenna [for inducing] *which induces* a radio frequency magnetic field in said at least a portion of said sample *in said chamber*, said radio frequency magnetic field substantially perpendicular to a magnetization direction of said static magnetic field;

circuits coupled to said antenna [for performing] *which perform* nuclear magnetic resonance spin echo measurements at a nuclear magnetic resonant frequency of carbon-13, said circuits including means for stacking said spin echo measurements over a measurement sequence; and a spectral analyzer [for measuring] *which measures* amplitudes of components of said spin echo measurements at frequency shifts of 30 and 130 parts per million from said resonant frequency.

6. The apparatus as defined in claim 5 further comprising:

at least one additional antenna switchably coupled to said circuits [for performing] *which perform* said nuclear magnetic resonance measurements, so that spin echo measurements can be performed during a wait time between measurements sequences performed using said first antenna on a portion of said fluid sample substantially unaffected by radio frequency magnetic fields radiated by said first antenna; and circuits [for stacking] *which stack* measurements made by said first antenna and said at least one additional antenna.

7. The apparatus as defined in claim 5 further comprising:

a sensor [for measuring] *which measures* a magnitude of said homogeneous static magnetic field induced by said magnets in said fluid sample *in said chamber*;

shim coils located proximal to said fluid sample, said shim coils inducing a selectable magnitude magnetic field on said fluid sample superimposed on said static magnetic field; and circuits [for imparting] *which impart* a direct current to said shim coils in response to an output of said sensor, said direct current adjusted by said circuits to maintain a substantially constant magnetic field amplitude in said fluid sample.

8. The apparatus as defined in claim 5 further comprising circuits selectively coupled to said antenna [for performing] *which perform* nuclear magnetic resonance spin echo measurements at a nuclear magnetic resonant frequency of hydrogen nuclei.

9. An apparatus [for characterizing] *which characterizes* a fluid sample withdrawn from an earth formation, comprising:

a probe [for selective hydraulic engagement with] *on a wireline instrument which selectively engages* said earth formation *using a hydraulic arrangement*;

a pump coupled to said probe [for] *which* selectively [withdrawing] *withdraws* said fluid sample from said formation; and a nuclear magnetic resonance sensor *in said wireline instrument* in hydraulic communication with said pump and said probe, said sensor comprising a magnet [for inducing] *which induces* a substantially homogeneous static magnetic field in *a chamber including* at least a portion of said sample, a first antenna [for inducing] *which induces* a radio frequency magnetic field in said at least a portion of said sample, said radio frequency magnetic field substantially perpendicular to a magnetization direction of said static magnetic field, circuits coupled to said antenna [for performing] *which perform* nuclear magnetic resonance spin echo measurements at a nuclear magnetic resonant frequency of carbon-13, said circuits [including means for] *enabling* stacking said spin echo measurements over a measurement sequence, and a spectral analyzer for measuring amplitudes of components of said spin echo measurements at frequency shifts of 30 and 130 parts per million from said resonant frequency.

10. The apparatus as defined in claim 9 further comprising:

at least one additional antenna switchably coupled to said circuits [for performing] *which perform* said nuclear magnetic resonance measurements, so that spin echo measurements can be performed during a wait time between measurements sequences performed using said first antenna on a portion of said fluid sample substantially unaffected by radio frequency magnetic fields radiated by said first antenna; and circuits [for stacking] *which stack* measurements made by said first antenna and said at least one additional antenna.

11. The apparatus as defined in claim 9 further comprising:

a sensor [for measuring] *which measures* a magnitude of said homogeneous static magnetic field induced by said magnets in said fluid sample *in said chamber*;

shim coils located proximal to said fluid sample, *wherein* said shim coils [for inducing] *induce* a selectable magnitude magnetic field on said fluid sample superimposed on said static magnetic field; and circuits for imparting a direct current to said shim coils in response to an output of said sensor, said direct current adjusted by said circuits to maintain a substantially constant magnetic field amplitude in said fluid sample *in said chamber*.

12. The apparatus as defined in claim 9 further comprising circuits selectively coupled to said antenna [for performing] *which perform* nuclear magnetic resonance spin echo measurements at a nuclear magnetic resonant frequency of hydrogen nuclei.

13. A method for characterizing a fluid sample withdrawn from an earth formation, comprising:

placing a probe in hydraulic communication with said earth formation, said probe forming part of an electric wireline formation testing instrument;

withdrawing fluid by operating a pump in selective hydraulic communication with said probe;

conducting said fluid into a sample chamber disposed in said instrument for performing nuclear magnetic resonance measurements on said fluid therein, said measurements comprising:

performing magnetic resonant spin echo measurements on said fluid sample *in said chamber* at a nuclear magnetic resonant frequency of carbon-13, summing amplitudes of said spin echo measurements, spectrally analyzing said summed amplitudes, and determining whether aromatic hydrocarbons are present in said fluid sample by measuring an amplitude of said spectrally analyzed summed amplitudes at about 130 part per million shift from said carbon-13 frequency; and determining whether aliphatic hydrocarbons are present in said fluid sample by measuring an amplitude of said spectrally analyzed summed amplitudes at about 30 parts per million frequency shift.

14. The method as defined in claim 13 further comprising improving a signal-to-noise ratio of said spin echo measurements by:

performing spin echo measurements on a first portion of said sample *in said chamber* during a wait time between sets of said spin echo measurements performed on a second portion of said sample *in said chamber*, said first portion substantially unaffected by a radio frequency magnetic field used to make said spin echo measurements on said second portion; and stacking said spin echo measurements made on said first portion and said second portion.

15. The method as defined in claim 13 further comprising measuring a magnitude of a static magnetic field *in said chamber* used to make said spin echo measurements and superimposing a selectable magnitude magnetic field on said static magnetic field to compensate for temperature induced changes in said magnitude of said static magnetic field.

16. The method as defined in claim 13 further comprising performing nuclear magnetic resonance spin echo amplitude measurements at a resonant frequency of hydrogen nuclei *in said chamber*, and determining a nuclear magnetic relaxation rate of said hydrogen nuclei.

17. The method as defined in claim 13 further comprising performing nuclear magnetic resonance spin echo measurements *in said chamber*, at a resonant frequency of sodium-23 ions in aqueous solution, summing amplitudes of said sodium-23 spin echo measurements, and determining a relative concentration of sodium ions in said fluid sample.

*18. A method for distinguishing between a first component and a second component in a fluid sample withdrawn from an earth formation and in a chamber on a wireline instrument, comprising:*

*(a) performing magnetic resonance spin echo measurements on said fluid sample in said chamber at a selected magnetic resonance frequency;*

*(b) summing amplitudes of said spin echo measurements;*

*(c) spectrally analyzing said summed amplitudes in the frequency domain;*

*(d) determining whether said first component is present in said fluid sample in said chamber by measuring an amplitude of said spectrally analyzed summed amplitudes at a shift characteristic of said first component from said selected resonant frequency; and*

*(e) determining whether said second component is present in said fluid sample in said chamber by measuring an amplitude of said spectrally analyzed summed amplitudes at a shift characteristic of said second component from said selected frequency.*

*19. The method as defined in claim 18 further comprising improving a signal-to-noise ratio of said spin echo measurements by:*

*(i) performing spin echo measurements on a first portion of said sample in said chamber during a wait time between sets of said spin echo measurements performed on a second portion of said sample in said chamber, said first portion substantially unaffected by a radio frequency magnetic field used to make said spin echo measurements on said second portion; and*

*(ii) stacking said spin echo measurements made on said first portion and said second portion.*

*20. The method as defined in claim 18 further comprising measuring a magnitude of a static magnetic field used to make said spin echo measurements in said chamber and superimposing a selectable magnitude magnetic field on said static magnetic field to compensate for temperature induced changes in said magnitude of said static magnetic field.*

*21. The method as defined in claim 18 further comprising performing nuclear magnetic resonance spin echo amplitude measurements at a resonant frequency of hydrogen nuclei in said chamber, and determining a relaxation rate of said hydrogen nuclei.*

*22. The method as defined in claim 18 wherein said selected magnetic resonance frequency is associated with carbon-13.*

*23. The method as defined in claim 18 wherein said first and second components comprise connate fluid and a mud filtrate.*

*24. An apparatus which characterizes a fluid sample withdrawn from an earth formation, said fluid sample contained within a chamber on a wireline instrument, the method comprising:*

*(a) a magnet on said wireline instrument which induces a substantially homogeneous static magnetic field in at least a portion of said sample in said chamber;*

*(b) a first antenna which induces a radio frequency magnetic field in said portion of said sample in said chamber, said radio frequency magnetic field substantially perpendicular to a magnetization direction of said static magnetic field;*

*(c) circuits coupled to said antenna which perform nuclear magnetic resonance spin echo measurements at a selected nuclear magnetic resonant frequency, said circuits including means for stacking said spin echo measurements over a measurement sequence; and*

*(d) a spectral analyzer which measures amplitudes of components of said spin echo measurements at frequency shifts characteristic of a first and second component of said fluid.*

*25. The apparatus as defined in claim 24 further comprising:*

*(i) at least one additional antenna switchably coupled to said circuits which performs said nuclear magnetic resonance measurements, so that spin echo measurements can be performed during a wait time between measurement sequences performed using said first antenna, on a portion of said fluid sample in said chamber that is substantially unaffected by radio frequency magnetic fields radiated by said first antenna; and*

*(ii) circuits which stack measurements made by said first antenna and said at least one additional antenna.*

*26. The apparatus as defined in claim 24 further comprising circuits selectively coupled to said antenna which perform nuclear magnetic resonance spin echo measurements at a nuclear magnetic resonant frequency of hydrogen nuclei.*

*27. The apparatus of claim 24 wherein said selected magnetic resonance frequency corresponds to carbon 13.*

*28. The method as defined in claim 24 wherein said first and second components comprise connate fluid and a mud filtrate.*

*29. A method which characterizes a fluid sample withdrawn from an earth formation, comprising:*

*(a) placing a probe in hydraulic communication with said earth formation, said probe forming part of a wireline formation testing instrument;*

*(b) withdrawing fluid by operating a pump in selective hydraulic communication with said probe;*

*(c) conducting said fluid into a sample chamber disposed in said instrument and performing nuclear magnetic resonance measurements on said fluid therein, said measurements comprising magnetic resonant spin echo measurements on said fluid sample in said sample chamber at a selected nuclear magnetic resonant*

*frequency, summing amplitudes of said spin echo measurements, and spectrally analyzing said summed amplitudes;*

(*d*) *determining whether a first component is present in said fluid sample by measuring an amplitude of said spectrally analyzed summed amplitudes at a frequency shift from said selected frequency characteristic of said first component; and*

(*e*) *determining whether a second component is present in said fluid sample by measuring an amplitude of said spectrally analyzed summed amplitudes at a frequency shift from said selected frequency characteristic of said second component.*

*30. The method of claim 29 wherein said selected frequency is associated with carbon-13.*

*31. The method of claim 29 wherein said first and second components comprise a connate fluid and a mud filtrate.*

* * * * *